(12) United States Patent
Mori et al.

(10) Patent No.: US 10,347,687 B2
(45) Date of Patent: Jul. 9, 2019

(54) IMAGING PANEL AND X-RAY IMAGING SYSTEM PROVIDED WITH SAID IMAGING PANEL

(71) Applicant: Sharp Kabushiki Kaisha, Osaka (JP)

(72) Inventors: Shigeyasu Mori, Osaka (JP); Kazuhide Tomiyasu, Osaka (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 377 days.

(21) Appl. No.: 15/320,712

(22) PCT Filed: Jun. 25, 2015

(86) PCT No.: PCT/JP2015/068303
§ 371 (c)(1),
(2) Date: Dec. 20, 2016

(87) PCT Pub. No.: WO2016/002610
PCT Pub. Date: Jan. 7, 2016

(65) Prior Publication Data
US 2017/0148843 A1    May 25, 2017

(30) Foreign Application Priority Data
Jun. 30, 2014 (JP) .................. 2014-134731

(51) Int. Cl.
*H01L 27/146* (2006.01)
*G01T 1/20* (2006.01)
(Continued)

(52) U.S. Cl.
CPC ....... *H01L 27/14663* (2013.01); *G01N 23/04* (2013.01); *G01T 1/20* (2013.01);
(Continued)

(58) Field of Classification Search
CPC ..... G01T 1/243; G01T 1/2002; G01T 1/2018; G01T 1/2012; H01L 27/14658; H01L 31/18; H01L 27/14663; G01N 23/04
See application file for complete search history.

(56) References Cited

U.S. PATENT DOCUMENTS

| 2004/0104351 A1 | 6/2004 | Shibayama |
| 2009/0057564 A1 | 3/2009 | Miyayama et al. |

(Continued)

FOREIGN PATENT DOCUMENTS

| JP | 2002-124676 A | 4/2002 |
| JP | 2006-156555 A | 6/2006 |

(Continued)

OTHER PUBLICATIONS

U.S. Appl. No. 15/320,682, filed Dec. 20, 2016.
(Continued)

*Primary Examiner* — Don K Wong
(74) *Attorney, Agent, or Firm* — ScienBiziP, P.C.

(57) ABSTRACT

An aim of the present invention is to improve the conversion efficiency of scintillation light into electric charge by a photoelectric conversion element in an imaging panel of an X-ray imaging system using an indirection conversion scheme. An imaging panel generates images based on scintillation light acquired from X-rays that have passed through a specimen. The imaging panel includes a substrate, thin film transistor, photoelectric conversion element, and reflective layer. The thin film transistor is formed on the substrate. The photoelectric conversion element is connected to the thin film transistor and converts incident scintillation light into electric charge. The entirety of a region of a light-receiving surface of the photoelectric conversion element where the scintillation light is incident overlaps the reflective layer as seen from the incident direction of the scintillation light. The reflective layer may be the drain electrode. Alternatively, the (Continued)

reflective layer may be a reflective electrode that is formed in the same layer as a gate electrode.

17 Claims, 9 Drawing Sheets

(51) Int. Cl.
*H04N 5/32* (2006.01)
*G01N 23/04* (2018.01)
*A61B 6/00* (2006.01)

(52) U.S. Cl.
CPC .. *H01L 27/14614* (2013.01); *H01L 27/14632* (2013.01); *H04N 5/32* (2013.01); *A61B 6/4233* (2013.01)

(56) References Cited

U.S. PATENT DOCUMENTS

| | | | |
|---|---|---|---|
| 2009/0078877 | A1 | 3/2009 | Yaegashi et al. |
| 2009/0250699 | A1 | 10/2009 | Okada |
| 2011/0133095 | A1 | 6/2011 | Imai |
| 2011/0186853 | A1 | 8/2011 | Terai et al. |
| 2012/0256095 | A1* | 10/2012 | Nakatsugawa ... H01L 27/14658 250/368 |
| 2012/0313103 | A1 | 12/2012 | Yamada et al. |
| 2013/0264485 | A1 | 10/2013 | Kawanabe et al. |
| 2013/0299711 | A1 | 11/2013 | Mochizuki et al. |
| 2013/0307041 | A1 | 11/2013 | Mochizuki et al. |
| 2014/0103347 | A1 | 4/2014 | Ishino |
| 2017/0131413 | A1 | 5/2017 | Tomiyasu et al. |
| 2017/0139056 | A1 | 5/2017 | Tomiyasu et al. |
| 2017/0154914 | A1 | 6/2017 | Tomiyasu et al. |
| 2017/0154915 | A1 | 6/2017 | Tomiyasu et al. |
| 2017/0154916 | A1 | 6/2017 | Mori et al. |
| 2017/0160403 | A1 | 6/2017 | Tomiyasu et al. |

FOREIGN PATENT DOCUMENTS

| | | |
|---|---|---|
| JP | 2006-253481 A | 9/2006 |
| JP | 2007-103578 A | 4/2007 |
| JP | 2009-59975 A | 3/2009 |
| JP | 2009-94465 A | 4/2009 |
| JP | 2009-212120 A | 9/2009 |
| JP | 2009-252835 A | 10/2009 |
| JP | 2010-98329 A | 4/2010 |
| JP | 2011-124334 A | 6/2011 |
| JP | 2011-159908 A | 8/2011 |
| JP | 2013-16772 A | 1/2013 |
| JP | 2013-219067 A | 10/2013 |
| JP | 2013-235934 A | 11/2013 |
| JP | 2013-235935 A | 11/2013 |
| JP | 2014-78651 A | 5/2014 |

OTHER PUBLICATIONS

U.S. Appl. No. 15/321,129, filed Dec. 21, 2016.
U.S. Appl. No. 15/320,704, filed Dec. 20, 2016.
U.S. Appl. No. 15/321,132, filed Dec. 21, 2016.
U.S. Appl. No. 15/321,127, filed Dec. 21, 2016.
U.S. Appl. No. 15/321,142, filed Dec. 20, 2016.
English machine translation of JP 2009-059975. (Listed by the U.S. Examiner in a PTO-892 form in the related U.S. Appl. No. 15/320,682.).

* cited by examiner

<A-A Cross Section>

US 10,347,687 B2

IMAGING PANEL AND X-RAY IMAGING SYSTEM PROVIDED WITH SAID IMAGING PANEL

TECHNICAL FIELD

The present invention relates to an imaging panel and X-ray imaging system, and more specifically to an imaging panel that generates images based on scintillation light from X-rays that have passed through a specimen, and an X-ray imaging system having this imaging panel.

BACKGROUND ART

There are X-ray imaging systems that capture images via an imaging panel having a plurality of pixels. X-ray imaging systems include direct conversion schemes and indirect conversion schemes.

In direct conversion schemes, an X-ray conversion film made of amorphous selenium (a-Se) converts incident X-rays into electric charge, for example. The converted electric charge is stored in a capacitor in the pixel. The stored electric charge is read out by operating a thin film transistor in the pixel. Image signals are generated based on the charge that is read out. Images are generated based on the image signals.

In indirect conversion schemes, a scintillator converts incident X-rays into scintillation light, for example. The scintillation light is converted to electric charge by a photoelectric conversion element in the pixel. The converted electric charge is read out by operating a thin film transistor in the pixel. Image signals are generated based on the charge that is read out. Images are generated based on the image signals.

SUMMARY OF THE INVENTION

An aim of the present invention is to improve the conversion efficiency of scintillation light into electric charge by the photoelectric conversion element in an imaging panel of an X-ray imaging system that uses an indirect conversion scheme.

An imaging panel of one embodiment of the present invention is an imaging panel for generating an image in accordance with scintillation light obtained from X-rays that have passed through a specimen, the imaging panel including: a substrate; a thin film transistor on the substrate; a photoelectric conversion element connecting to the thin film transistor and converting the scintillation light that is received to electric charge; and a reflective layer that, as seen from a radiation direction of the scintillation light, overlaps an entirety of a region of a light-receiving surface of the photoelectric conversion element where the scintillation light is received, wherein the thin film transistor includes: a gate electrode on the substrate; a first insulating film covering the gate electrode; a semiconductor active layer on the first insulating film; and a drain electrode on the first insulating film and connected to the semiconductor active layer and the photoelectric conversion element, wherein the reflective layer is a reflective electrode in a same layer as the drain electrode or the gate electrode.

In an imaging panel of an embodiment of the present embodiment, it is possible to improve the conversion efficiency of scintillation light into electric charge by the photoelectric conversion element.

DETAILED DESCRIPTION OF EMBODIMENTS

Figure 1:
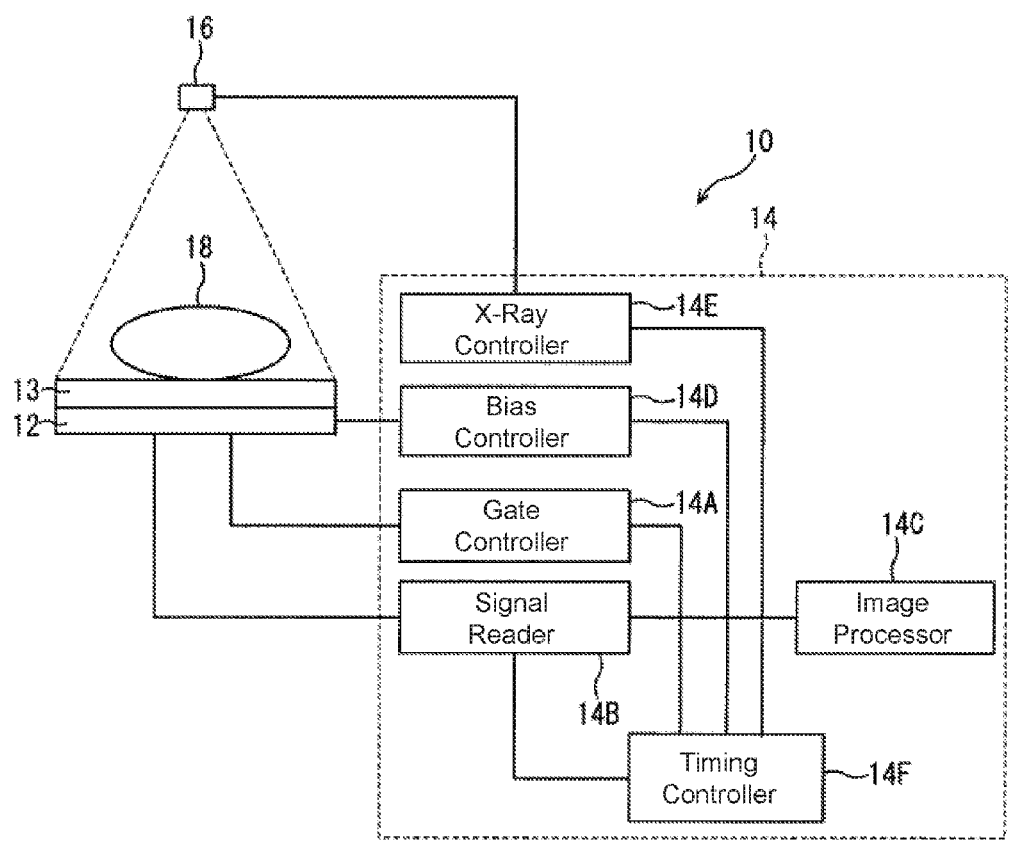
FIG. 1 is a schematic view of a general configuration of an X-ray imaging system according to Embodiment 1 of the present invention.

An imaging panel of one embodiment of the present invention is an imaging panel for generating an image in accordance with scintillation light obtained from X-rays that have passed through a specimen, the imaging panel including: a substrate; a thin film transistor on the substrate; a photoelectric conversion element connecting to the thin film transistor and converting the scintillation light that is received to electric charge; and a reflective layer that, as seen from a radiation direction of the scintillation light, overlaps an entirety of a region of a light-receiving surface of the photoelectric conversion element where the scintillation light is received, wherein the thin film transistor includes: a gate electrode on the substrate; a first insulating film covering the gate electrode; a semiconductor active layer on the first insulating film; and a drain electrode on the first insulating film and connected to the semiconductor active layer and the photoelectric conversion element, wherein the reflective layer is a reflective electrode in a same layer as the drain electrode or the gate electrode.

In the imaging panel described above, the reflective layer reflects scintillation light that has passed through the photoelectric conversion element. The reflected scintillation light enters the photoelectric conversion element.

In the imaging panel, the entirety of the region of the light-receiving surface of the photoelectric conversion element where the scintillation light is incident overlaps the reflective layer as seen from the incident direction of the scintillation light. Thus, the amount of scintillation light that enters the photoelectric conversion element can be increased, as compared to if the entirety of the region of the light-receiving surface of the photoelectric conversion element where the scintillation light is incident did not overlap the reflective layer as seen from the incident direction of the scintillation light. As a result, it is possible to increase the conversion efficiency of scintillation light into electric charge by the photoelectric conversion element.

The material of the reflective layer has no particular limitations as long as the material can reflect the scintillation light, but the material is preferably metal. When the reflective layer is the drain electrode, it is not necessary to provide a separate reflective layer. When the reflective layer is a reflective electrode, the drain electrode is a transparent conductive film. The reflective electrode is preferably made of the same material as the gate electrode.

In the imaging panel, it is preferable that the light-receiving surface of the photoelectric conversion element have a recess. In such a case, it is possible to increase the light-receiving surface area of the photoelectric conversion element.

It is preferable that an opening area of the recess be larger near the light-receiving surface than near a bottom of the recess. In such a case, it is easier for scintillation light to enter the light-receiving surface.

It is preferable that the semiconductor active layer be made of an oxide semiconductor. In such a case, it is possible to achieve high resolution images. The reason for this is as follows.

In a thin film transistor where the semiconductor active layer is made of an oxide semiconductor, the ON current is approximately 20 times greater than conventional thin film transistors, and the OFF current (leakage current) is several orders of magnitude smaller than conventional thin film transistors. Because the ON current is larger, it is possible to reduce the size of the thin film transistor. Because the OFF current is smaller, it is possible to reduce the area of the storage capacitor. As a result, pixel pitch can be reduced, which allows for higher resolution.

The oxide semiconductor is an oxide containing prescribed proportions of indium (In), gallium (Ga), and zinc (Zn), for example.

The thin film transistor further includes a second insulating film covering the semiconductor active layer, and the first insulating film and the second insulating film preferably include a silicon oxide film contacting the semiconductor active layer.

Silicon oxide films contain less hydrogen than silicon nitride films. Therefore, reducing the hydrogen contained in the semiconductor active layer makes it possible to prevent negative effects on the characteristics of the thin film transistor.

An X-ray imaging system of one embodiment of the present invention includes the imaging panel; an X-ray source; and a scintillator between the imaging panel and the X-ray source.

Due to using the imaging panel described above, the conversion efficient of scintillation light into electric charge by the photoelectric conversion element can be improved.

Specific embodiments of the present invention will be explained below with reference to figures. Portions in the drawings that are the same or similar are assigned the same reference characters and descriptions thereof will not be repeated.

<Embodiment 1>

FIG. 1 shows an X-ray imaging system 10 according to Embodiment 1 of the present invention. The X-ray imaging system 10 includes an imaging panel 12, scintillator 13, controller 14, and X-ray source 16.

In the X-ray imaging system 10, X-rays are radiated from the X-ray source 16, and X-rays that have passed through a specimen 18 enter the scintillator 13. The scintillator 13 emits fluorescent light (scintillation light) when irradiated by the X-rays. The imaging panel 12 and controller 14 capture the scintillation light in order to acquire an image.

Figure 2A:
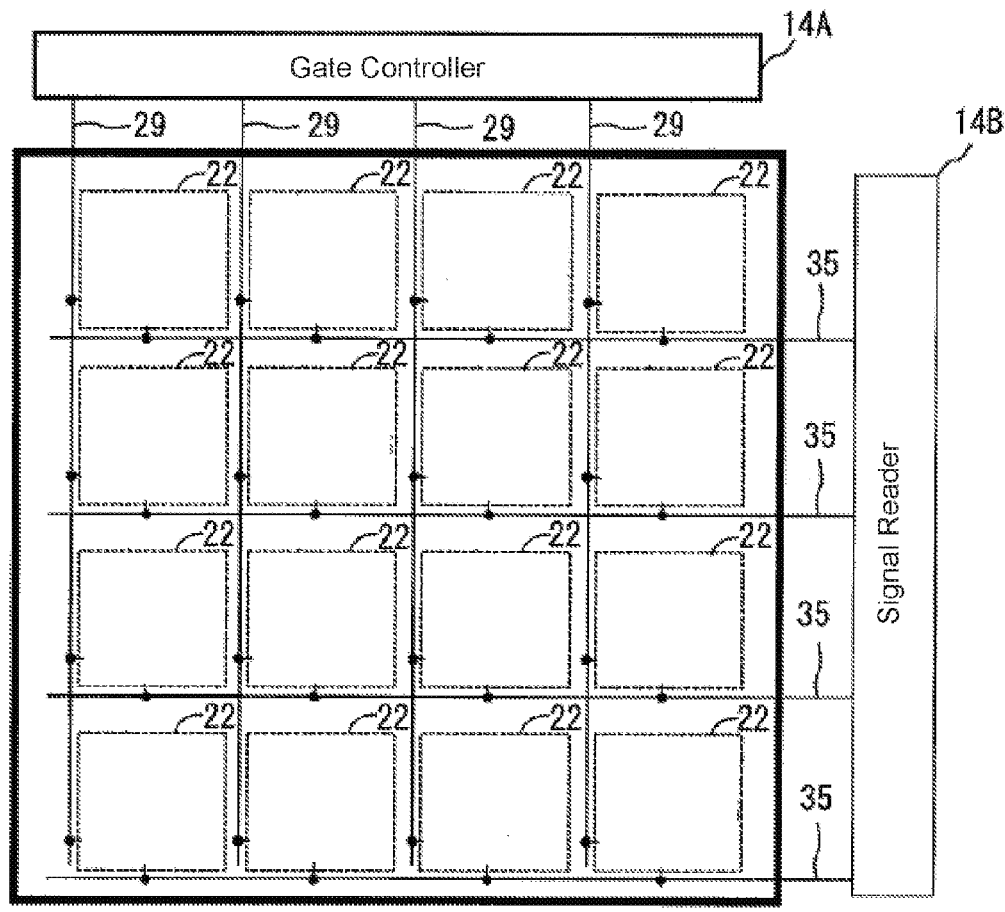
FIG. 2A is a schematic view of the arrangement of a plurality of pixels in the imaging panel.

As shown in FIG. 2A, the imaging panel 12 includes a plurality of pixels 22. As shown in FIG. 2A, the plurality of pixels 22 are arranged in a matrix pattern. In the example shown in FIG. 2A, sixteen pixels 22 are arranged in 4 rows×4 columns. The pixels 22 output signals (light detection signals) that correspond to the intensity of incident scintillation light.

Figure 3:
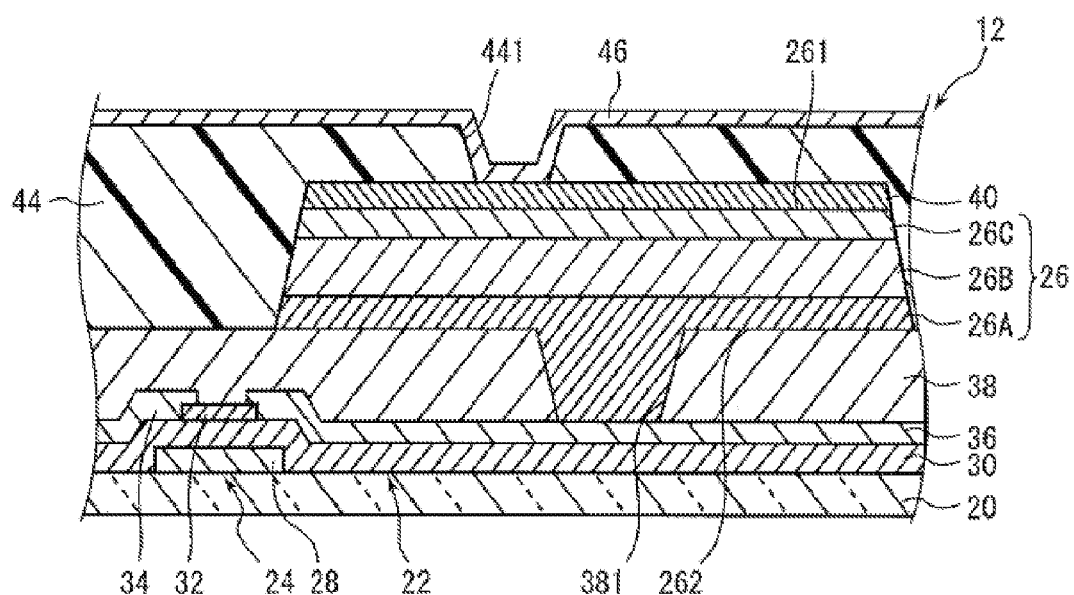
FIG. 3 is a cross-sectional view of FIG. 4 along A-A and shows a cross section of a general configuration of the pixel.

FIG. 3 is a cross-sectional view of a general configuration of one of the pixels 22 of the imaging panel 12. The pixel 22 is formed on a substrate 20 in the imaging panel 12. The substrate 20 has no particular limitations as long as the substrate is an insulating substrate. The substrate 20 may be a glass substrate, for example, or a compound resin substrate. The compound resin may be polyethylene terephthalate (PET), polyethylene naphthalate (PEN), polyether sulfone (PES), an acrylic resin, a polyimide, or the like, for example.

Figure 2B:
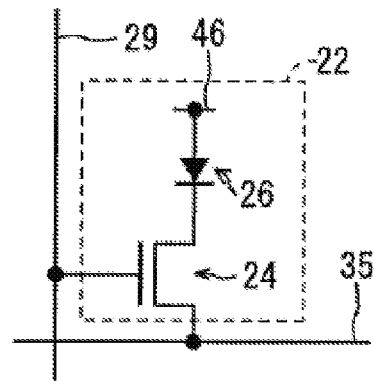
FIG. 2B is an equivalent circuit of a pixel.

As shown in FIG. 2B, the pixel 22 includes a thin film transistor 24, and a photodiode 26 as a photoelectric conversion element.

As shown in FIG. 3, the thin film transistor 24 includes a gate electrode 28, gate insulating film 30, semiconductor active layer 32, source electrode 34, and drain electrode 36.

Figure 4:
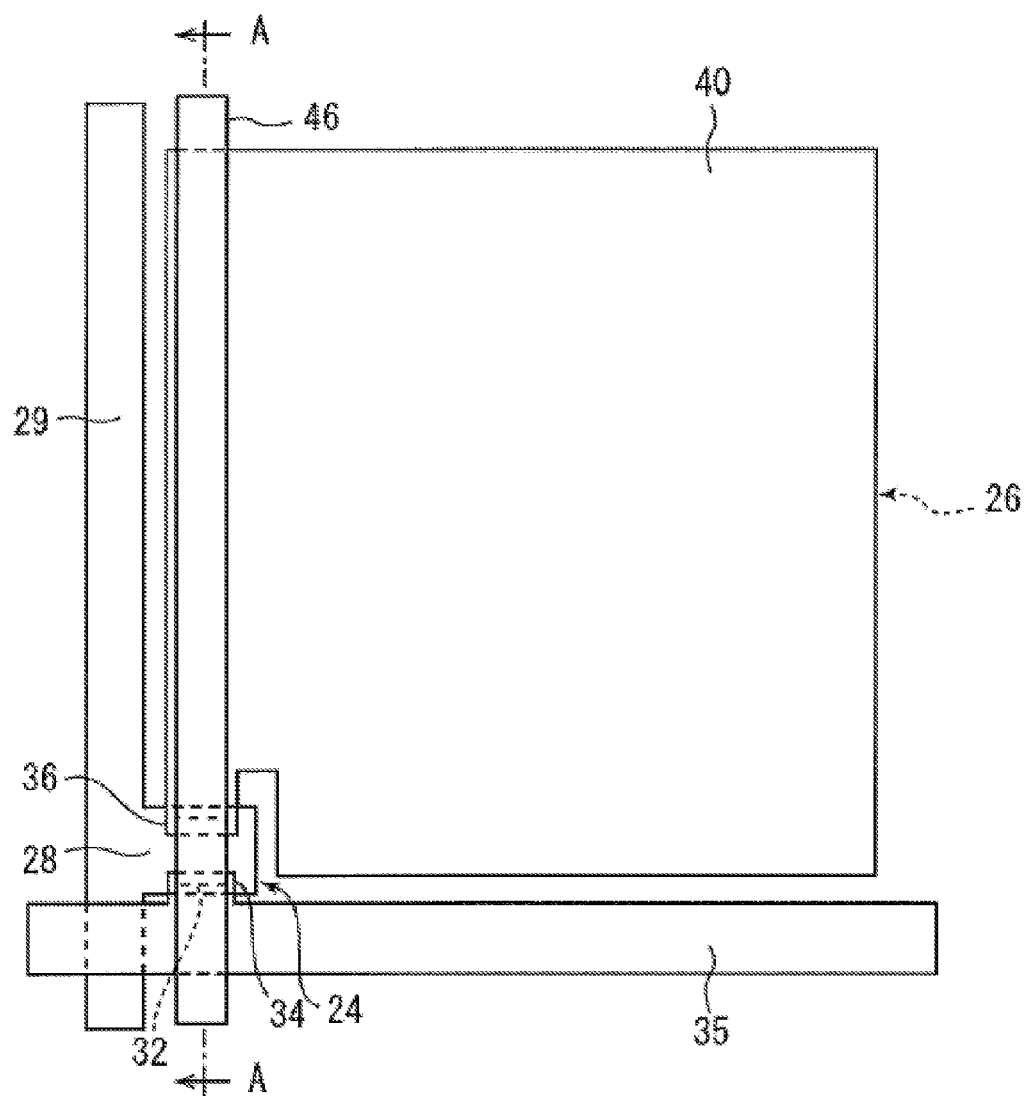
FIG. 4 is a plan view of a general configuration of the pixel.

As shown in FIG. 3, the gate electrode 28 is formed contacting one surface (hereinafter, main surface) of the substrate 20 in the thickness direction. The gate electrode 28 is formed of a metal such as aluminum (Al), tungsten (W), molybdenum (Mo), tantalum (Ta), chromium (Cr), titanium (Ti), or copper (Cu), for example, or alternatively is a nitride of these metals. Alternatively, the gate electrode 28 may be a plurality of metal films layered together, for example. In the present embodiment, the gate electrode 28 has a multi-layer structure in which a titanium metal film, aluminum metal film, and titanium metal film are layered together in this order. The gate electrode 28 is formed by using sputtering or the like to form a metal film on the substrate 20 and then patterning this metal film via photolithography, for example. The thickness of the gate electrode 28 is 50 nm to 300 nm, for example. The gate electrode 28 may be constituted by a gate line formed on the substrate 20 and extending in a prescribed direction, or alternatively the gate electrode may be constituted by a portion extending from the gate line in a direction that differs from the prescribed direction. As shown in FIG. 4, in the present embodiment, the gate electrode 28 is constituted by a portion extending from a gate line 29.

As shown in FIG. 3, the gate insulating film 30 is formed on the substrate 20 and covers the gate electrode 28. The gate insulating film 30 includes a silicon nitride film and a silicon oxide film, for example. The silicon nitride film is formed contacting the gate electrode 28 and substrate 20. The silicon oxide film is formed contacting the silicon nitride film. The thickness of the silicon nitride film is 100 nm to 400 nm, for example. The thickness of the silicon oxide film is 50 nm to 100 nm, for example. The gate insulating film 30 is formed by plasma-enhanced CVD, for example. In order to form a precise insulating film with low gate leakage current at a low temperature, a noble gas element such as argon may be included in the reactive gas and mixed into the insulating film. The gate insulating film 30 may alternatively be constituted by only the silicon oxide film. Instead of a silicon nitride film, the insulating film may be a silicon nitride oxide film ($SiN_xO_y$) (x>y). Instead of a silicon oxide film, the insulating film may be a silicon oxynitride film ($SiO_xN_y$) (x>y).

As shown in FIG. 3, the semiconductor active layer 32 is formed contacting the gate insulating film 30. The semiconductor active layer 32 is an oxide semiconductor. The oxide semiconductor is an oxide containing prescribed proportions of indium (In), gallium (Ga), and zinc (Zn), for example.

The oxide semiconductor may be InGaO$_3$ (ZnO)$_5$, magnesium zinc oxide (Mg$_x$Zn$_{1-x}$O), cadmium zinc oxide (Cd$_x$Zn$_{1-x}$O), cadmium oxide (CdO), or an In—Ga—Zn—O amorphous oxide semiconductor (a-IGZO), for example. The oxide semiconductor may be non-crystalline, polycrystalline, or microcrystalline ZnO having a mix of non-crystalline and polycrystalline states, or a material that has had no impurity elements added to this ZnO. The impurity element is one or multiple elements selected from group 1 elements, group 13 elements, group 14 elements, group 15 elements, or group 17 elements, for example. The thickness of the semiconductor active layer 32 is 30 nm to 100 nm, for example. The semiconductor active layer 32 is formed by forming a semiconductor layer via sputtering or the like and then using photolithography to pattern the semiconductor layer, for example. After the semiconductor layer has been formed, or after the semiconductor active layer 32 has been formed, a high-temperature heat treatment (350° C. or greater, for example) may be performed in an environment containing oxygen (e.g., the atmosphere). In such a case, it is possible to reduce oxygen defects in the oxide semiconductor layer.

As shown in FIG. 3, the source electrode 34 and drain electrode 36 are formed contacting the semiconductor active layer 32 and gate insulating film 30. As shown in FIG. 4, the source electrode 34 is connected to the source line 35. The source electrode 34, source line 35, and drain electrode 36 are formed on the same layer. The source electrode 34, source line 35, and drain electrode 36 are formed of a metal such as aluminum (Al), tungsten (W), molybdenum (Mo), tantalum (Ta), chromium (Cr), titanium (Ti), or copper (Cu), for example, or alternatively is a nitride of these metals. The source electrode 34, source line 35, and drain electrode 36 may be a plurality of metal films layered together, for example. In the present embodiment, the source electrode 34, source line 35, and drain electrode 36 have a multilayer structure in which a titanium metal film, aluminum metal film, and titanium metal film are layered together in this order. The thickness of the source electrode 34, source line 35, and drain electrode 36 is 50 nm to 500 nm, for example. The source electrode 34, source line 35, and drain electrode 36 are formed by using sputtering or the like to form a metal film on the semiconductor active layer 32 and gate insulating film 30 and then patterning this metal film via photolithography, for example. The etching when patterning the metal film may be dry etching or may be wet etching. When etching a metal film formed on a substrate with a wide area, it is preferable to use dry etching (anisotropic etching), which has less line width shifts, or namely less variation in line width.

As shown in FIG. 3, the imaging panel 12 further includes an insulating film 38. The insulating film 38 covers the semiconductor active layer 32, source electrode 34, source line 35, and drain electrode 36. The insulating film 38 functions as a passivation film. The insulating film 38 is a silicon oxide film, for example. The insulating film 38 may be a silicon nitride film, or alternatively may be a silicon nitride film and silicon oxide film that have been layered together. The thickness of the insulating film 38 is 50 nm to 300 nm, for example. The insulating film 38 is formed by plasma-enhanced CVD, for example.

After the insulating film 38 has been formed, a heat treatment may be performed at a temperature of approximately 350 degrees. In such a case, it is possible to reduce defects in the insulating film 38.

The insulating film 38 has formed therein a contact hole 381. The contact hole 381 overlaps the drain electrode 36 when seen from a direction perpendicular to the main surface of the substrate 20. The contact hole 381 is formed by photolithography, for example.

As shown in FIG. 3, the photodiode 26 is connected to the drain electrode 36 via the contact hole 381. The entirety of the photodiode 26 overlaps the drain electrode 36 when seen from the direction perpendicular to the main surface of the substrate 20. The photodiode 26 includes an n-type amorphous silicon layer 26A, an intrinsic amorphous silicon layer 26B, and a p-type amorphous silicon layer 26C.

The n-type amorphous silicon layer 26A is made of amorphous silicon that has been doped by an n-type impurity (phosphorous, for example). The n-type amorphous silicon layer 26A is formed contacting the drain electrode 36. The thickness of the n-type amorphous silicon layer 26A is 20 nm to 100 nm, for example.

The intrinsic amorphous silicon layer 26B is made of intrinsic amorphous silicon. The intrinsic amorphous silicon layer 26B is formed contacting the n-type amorphous silicon layer 26A. The thickness of the intrinsic amorphous silicon layer 26B is 200 nm to 2000 nm, for example.

The p-type amorphous silicon layer 26C is made of amorphous silicon that has been doped by a p-type impurity (boron, for example). The p-type amorphous silicon layer 26C is formed contacting the intrinsic amorphous silicon layer 26B. The thickness of the p-type amorphous silicon layer 26C is 10 nm to 50 nm, for example.

The photodiode 26 is formed by plasma-enhanced CVD of the n-type amorphous silicon film, intrinsic amorphous silicon film, and p-type amorphous silicon film in this order, for example. Thereafter, these films are patterned via photolithography. This results in the forming of the photodiode 26.

As shown in FIG. 3, the imaging panel 12 further includes an electrode 40. The electrode 40 is formed contacting the p-type amorphous silicon layer 26C of the photodiode 22. The electrode 40 covers all of the p-type amorphous silicon layer 26C. In other words, the electrode 40 covers the entirety of a light-receiving surface 261 of the photodiode 26. The electrode 40 is a transparent conductive film, for example. The transparent conductive film is indium zinc oxide, for example. The electrode 40 is formed by forming the transparent conductive film via sputtering or the like and then patterning this transparent conductive film via photolithography, for example. The thickness of the electrode 40 is 50 nm to 500 nm, for example.

As shown in FIG. 3, the imaging panel 12 further includes a planarizing film 44. The planarizing film 44 is made of a photosensitive resin, for example. The planarizing film 44 covers the insulating film 38 and electrode 40. The thickness of the planarizing film 44 is 1000 nm to 4000 nm, for example. The planarizing film 44 is formed by spin coating, slit coating, or the like, and then a thermal treatment thereafter in a 150 to 250 degree atmosphere, for example. The thermal treatment temperature when curing the planarizing film 44 differs depending on the material of the planarizing film 44. The planarizing film 44 has formed therein a contact hole 441. The contact hole 441 overlaps the electrode 40 when seen from the direction perpendicular to the main surface of the substrate 20. The contact hole 441 is formed by photolithography, for example.

As shown in FIGS. 3 and 4, the imaging panel 12 further includes a wiring line 46. The wiring line 46 is formed on the planarizing film 44. As shown in FIG. 4, the wiring line 46 extends parallel to the source line 35. The wiring line 46 overlaps the semiconductor active layer 32 when seen from the direction perpendicular to the main surface of the substrate 20. As shown in FIG. 4, in the present embodiment, the wiring line 46 overlaps the portion of the semiconductor active layer 32 not contacting the source electrode 34 and drain electrode 36 when seen from the direction perpendicular to the main surface of the substrate 20. As shown in FIG. 4, in the present embodiment, the wiring line 46 overlaps the portion of the semiconductor active layer 32 overlapping the gate electrode 28 when seen from the direction perpendicular to the main surface of the substrate 20. As shown in FIG. 4, the wiring line 46 overlaps the electrode 40 when seen from the direction perpendicular to the main surface of the substrate 20. The wiring line 46 is made of a metal such as aluminum (Al), tungsten (W), molybdenum (Mo), tantalum (Ta), chromium (Cr), titanium (Ti), or copper (Cu), or is an alloy of these metals or a metal nitride of these, for example. The wiring line 46 may be a transparent conductive film, for example. The transparent conductive film is indium zinc oxide, for example. The wiring line 46 contacts the electrode 40 via the contact hole 441. The thickness of the wiring line 46 is 50 nm to 500 nm, for example. The wiring line 46 is formed by forming a conductive film via sputtering or the like and then patterning this conductive film via photolithography, for example.

As shown in FIG. 1, the controller 14 includes a gate controller 14A, signal reader 14B, image processor 14C, bias controller 14D, X-ray controller 14E, and timing controller 14F. In FIG. 1, the controller 14 is provided separately from the imaging panel 12, but alternatively, a portion or all of the controller 14 may be provided in the imaging panel 12.

As shown in FIG. 2A, the gate controller 14A is connected to a plurality of gate lines 29. Several of the plurality of pixels 22 are connected to each of the gate lines 29. In the example shown in FIG. 2A, four of the pixels 22 are connected to each of the gate lines 29. The gate controller 14A selects one gate line 29 from the plurality of gate lines 29 based on the control signal from the timing controller 14F. The gate controller 14A applies, via the selected gate line 29, a prescribed gate voltage to the thin film transistor 24 of the pixel 22 connected to the corresponding gate line 29 (see FIG. 2B).

As shown in FIG. 2A, the signal reader 14B is connected to the plurality of source lines 35. Several of the plurality of pixels 22 are connected to each of the source lines 35. In the example shown in FIG. 2A, four of the pixels 22 are connected to each of the source lines 35. The signal reader 14B selects one source line 35 from the plurality of source lines 35 based on the control signal from the timing controller 14F. The signal reader 14B reads out light detection signals from the photodiode 26 (see FIG. 2B) via the selected source line 35. The light detection signals correspond to the electric charge generated by the photodiode 26 when scintillation light enters the photodiode 26. In other words, the magnitude of the light detection signal changes in accordance with the amount of electrical charge generated by the photodiode 26. The pixel 22 for which the light detection signal is read out is connected to the source line 35 selected by the signal reader 14B and connected to the gate line 29 selected by the gate controller 14A. The signal reader 14B generates image signals based on the read out light detection signals and outputs the result to the image processor 14C.

The image processor 14C generates images based on the image signals output from the signal reader 14B.

The bias controller 14D is connected to the wiring line 46. The bias controller 14D applies a prescribed voltage to the wiring line 46 when the X-rays are being irradiated based on the control signal from the timing controller 14F. This applies a bias voltage to the photodiode 26. This results in the expansion of a depletion layer in the photodiode 26.

The X-ray controller 14E controls the radiation of X-rays by the X-ray source 16 based on the control signal from the timing controller 14F.

The timing controller 14F controls the operation timing of the gate controller 14A, signal reader 14B, bias controller 14D, and X-ray controller 14E.

In the X-ray imaging system 10, the X-rays radiated from the X-ray source 16 irradiate the scintillator 13 via the specimen 18. The X-rays that have irradiated the scintillator 13 are converted to scintillation light. The scintillation light enters the photodiode 26. This generates a light detection signal. At such time, the thin film transistor 24 turns ON, and the light detection signal is read out. An image signal is generated based on the light detection signal that is read out. An image is generated based on the generated image signal.

In the imaging panel 12 of the X-ray imaging system 10, the entirety of the photodiode 26 overlaps the drain electrode 36 as seen from the direction perpendicular to the main surface of the substrate 20, or namely the entering direction of the scintillation light into the photodiode 26. Thus, the scintillation light that has entered the photodiode 26 and passed through the photodiode 26 can be reflected by the drain electrode 36. The scintillation light that has been reflected by the drain electrode 36 enters the photodiode 26. In other words, in the photodiode 26, the surface 262 opposite to the light-receiving surface 261 also functions as a light-receiving surface. The scintillation light that has been reflected by the drain electrode 36 enters the photodiode 26, which improves the usage efficiency of the scintillation light. Namely, the light detection sensitivity of the photodiode 26 is improved.

As shown in FIG. 4, in the imaging panel 12, the thin film transistor 24 is positioned near the intersection of the gate line 29 and source line 35 as seen from the direction perpendicular to the main surface of the substrate 20. The wiring line overlaps the semiconductor active layer 32. Therefore, when the wiring line 46 is made of metal, for example, then it is possible to secure a greater light-receiving area of the photodiode 26, as compared to if the wiring line 46 did not overlap the semiconductor active layer 32. As a result, the light detection sensitivity of the photodiode 26 is improved.

<Application Example of Embodiment 1>

Figure 5:
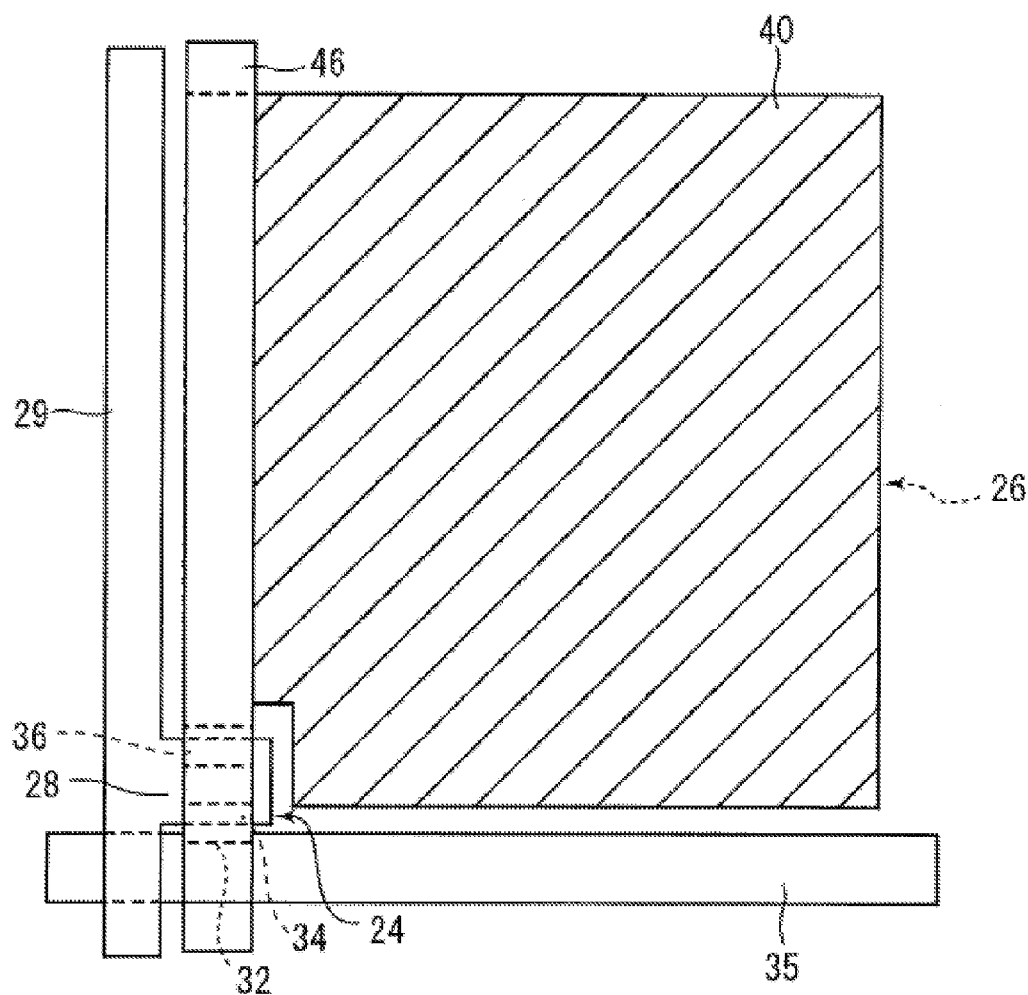
FIG. 5 is a plan view of a schematic configuration of a pixel according to an application example of Embodiment 1.

The entirety of the photodiode 26 need not overlap the drain electrode 36 as seen from the entrance direction of the scintillation light into the photodiode 26. When the wiring line 46 is made of metal, for example, the photodiode need only overlap the diagonal line section in FIG. 5, or namely the region of the light-receiving surface of the photodiode 26 where scintillation light is incident.

<Embodiment 2>

Figure 6:
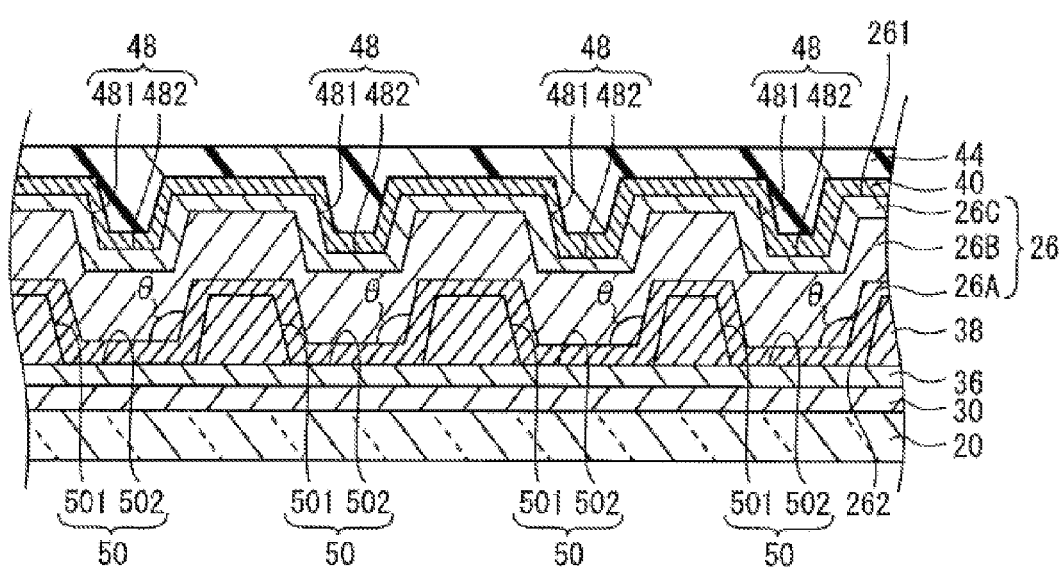
FIG. 6 is a cross-sectional view of a schematic configuration of a photodiode used in Embodiment 2 of the present invention.
Figure 7:
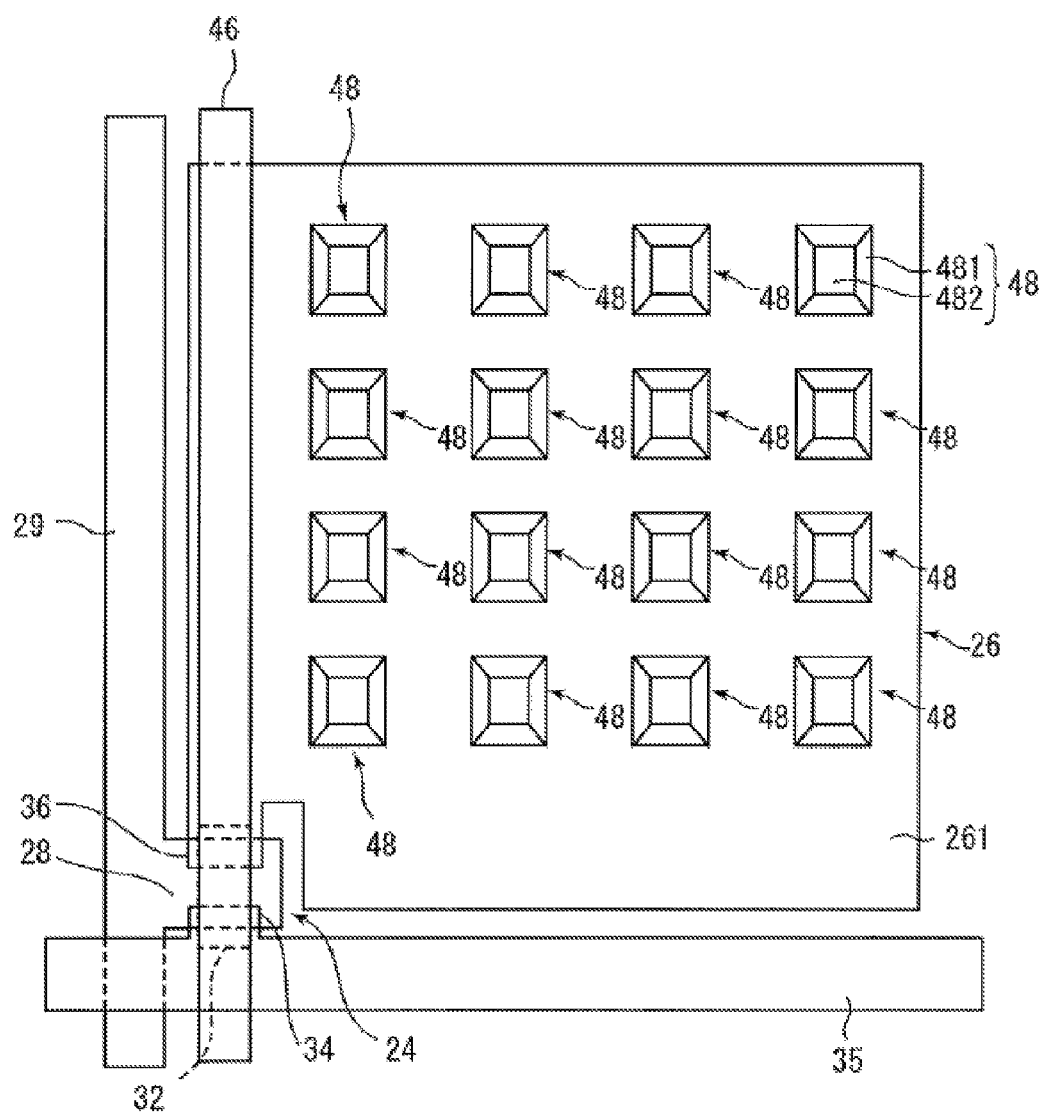
FIG. 7 is a plan view of one example of the positioning of the recesses in the light-receiving surface of the photodiode.
Figure 8:
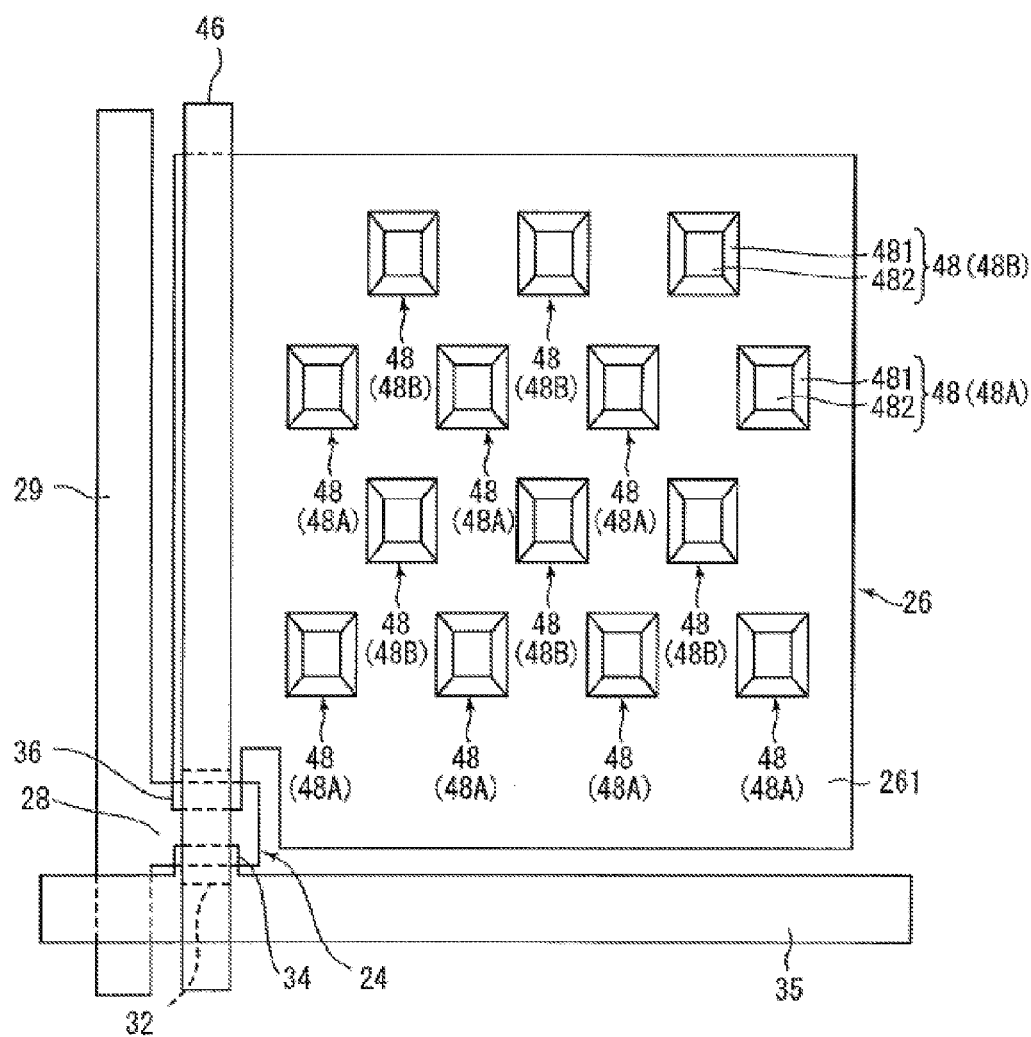
FIG. 8 is a plan view of another example of the positioning of the recesses in the light-receiving surface of the photodiode.

A photodiode 27 used in Embodiment 2 of the present invention will be explained with reference to FIGS. 6 and 7. As shown in FIG. 6, the photodiode 27 has a plurality of recesses 48 formed in the light-receiving surface 261. As shown in FIG. 7, the plurality of recesses 48 are arranged in a matrix pattern. In FIG. 7, for ease of understanding, an example is shown without the electrode 40. In the example shown in FIG. 7, the plurality of recesses 48 are arranged in 4 rows×4 columns. As shown in FIG. 8, it is possible to differ the number of recesses 48 (first recesses 48A) constituting one of the two adjacent rows from the number of recesses (second recesses 48B) constituting the other row, and it is also possible to differ the positions in the row direction of the first recesses 48A from the positions in the row direction of the second recesses 48B. In FIG. 8, for ease of understanding, an example is shown without the electrode 40, in a similar manner to FIG. 7.

As shown in FIG. 6, the recess 48 has a side face 481 and a bottom surface 482. The side face 481 is slanted towards the bottom surface 482. The angle θ of the slant is greater than 90 degrees. In other words, the aperture area of the recess 48 is greater near the light-receiving surface 261 than the bottom surface 482.

As shown in FIG. 7, the aperture shape of the recesses 48 is rectangular. The aperture shape of the recesses 48 may alternatively be polygonal or circular.

To form the recesses 48, the photodiode 27 can be formed on the insulating film 38 after a hole 50 has been formed in the insulating film 38. The side face 481 of the recess 48 corresponds to a side face 501 of the hole 50. Accordingly, if the side face 501 of the hole 50 is slanted towards the bottom surface 502 of the hole 50 (i.e., towards the surface of the drain electrode 36), then it is possible to form the desired recess 48. To slant the side face 501 toward the bottom surface 502, the relationship between the anisotropic components and isotropic components during dry etching should be set as appropriate, for example.

In the present embodiment, there are recesses and protrusions on the light-receiving surface 261 of the photodiode 27. Thus, it is possible to increase the surface area of the light-receiving surface 261. Therefore, it is possible to improve the light detection sensitivity of the photodiode 27.

In the present embodiment, in the photodiode 27, the surface 262 opposite to the light-receiving surface 261 also functions as a light-receiving surface, and recesses and protrusions are also formed in this surface 262. As a result, it is possible to increase the surface area of the light-receiving surface (the surface 262 described above) when the scintillation light that has been reflected by the drain electrode 36 enters the photodiode 26. Therefore, it is possible to further improve the light detection sensitivity of the photodiode 27.

<Embodiment 3>

Figure 9:
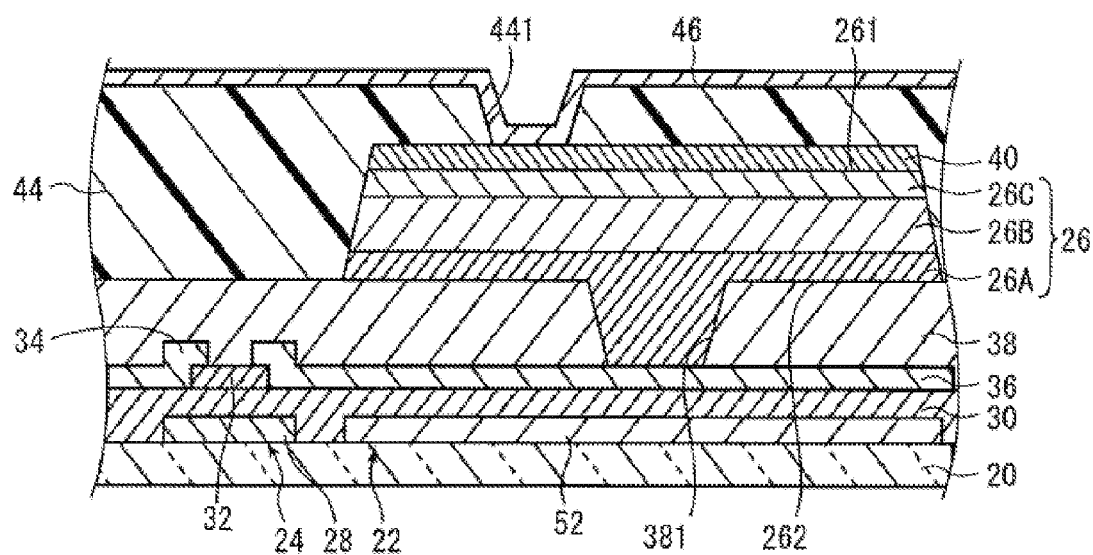
FIG. 9 is a cross-sectional view of a reflective layer used in Embodiment 3 of the present invention.

A reflective layer 52 used in Embodiment 3 of the present invention will be explained with reference to FIG. 9. The reflective layer 52 is formed in the same layer as the gate electrode 28. In other words, the reflective layer 52 is formed on the main surface of the substrate 20. The reflective layer 52 is formed of the same material as the gate electrode 28. The drain electrode 36 is a transparent conductive film. The reflective layer 52 is positioned below the drain electrode 36 of each thin film transistor 24. Each of the reflective layers 52 are connected to one another via suitable wiring lines.

In the present embodiment, the reflective layer 52 reflects scintillation light that has passed through the photodiode 26 to cause this scintillation light to enter the photodiode 26. Thus, effects and results similar to Embodiment 1 can be achieved.

The embodiments of the present invention have been described above. However, these are merely examples, and the present invention is not at all limited by the embodiments described above.

What is claimed is:

1. An imaging panel for generating an image in accordance with scintillation light obtained from X-rays that have passed through a specimen, the imaging panel comprising:
   a substrate;
   a thin film transistor on the substrate;
   a photoelectric conversion element connecting to the thin film transistor and converting the scintillation light that is received to electric charge; and
   a reflective layer that, as seen from a radiation direction of the scintillation light, overlaps an entirety of a region of a light-receiving surface of the photoelectric conversion element where the scintillation light is received,
   wherein the thin film transistor includes:
      a gate electrode on the substrate;
      a first insulating film covering the gate electrode;
      a semiconductor active layer on the first insulating film; and
      a drain electrode on the first insulating film and connected to the semiconductor active layer and the photoelectric conversion element,
   wherein the reflective layer is a reflective electrode in a same layer as the drain electrode or the gate electrode.

2. The imaging panel according to claim 1, wherein the light-receiving surface of the photoelectric conversion element has a recess.

3. The imaging panel according to claim 2, wherein an opening area of said recess is larger near the light-receiving surface than near a bottom of the recess.

4. The imaging panel according to claim 1, wherein the semiconductor active layer is made of an oxide semiconductor.

5. The imaging panel according to claim 4, wherein the oxide semiconductor is an oxide containing prescribed proportions of indium (In), gallium (Ga), and zinc (Zn).

6. The imaging panel according to claim 4,
   wherein the thin film transistor further includes a second insulating film covering the semiconductor active layer, and
   wherein the first insulating film and the second insulating film include a silicon oxide film contacting the semiconductor active layer.

7. An X-ray imaging system, comprising:
   the imaging panel according to claim 1;
   an X-ray source; and
   a scintillator between the imaging panel and the X-ray source.

8. The imaging panel according to claim 2, wherein the semiconductor active layer is made of an oxide semiconductor.

9. The imaging panel according to claim 3, wherein the semiconductor active layer is made of an oxide semiconductor.

10. The imaging panel according to claim 8, wherein the oxide semiconductor is an oxide containing prescribed proportions of indium (In), gallium (Ga), and zinc (Zn).

11. The imaging panel according to claim 9, wherein the oxide semiconductor is an oxide containing prescribed proportions of indium (In), gallium (Ga), and zinc (Zn).

12. The imaging panel according to claim 8,
   wherein the thin film transistor further includes a second insulating film covering the semiconductor active layer, and
   wherein the first insulating film and the second insulating film include a silicon oxide film contacting the semiconductor active layer.

13. The imaging panel according to claim 9,
   wherein the thin film transistor further includes a second insulating film covering the semiconductor active layer, and wherein the first insulating film and the second insulating film include a silicon oxide film contacting the semiconductor active layer.

14. The imaging panel according to claim 5,
wherein the thin film transistor further includes a second insulating film covering the semiconductor active layer, and
wherein the first insulating film and the second insulating film include a silicon oxide film contacting the semiconductor active layer.

15. The imaging panel according to claim 10,
wherein the thin film transistor further includes a second insulating film covering the semiconductor active layer, and
wherein the first insulating film and the second insulating film include a silicon oxide film contacting the semiconductor active layer.

16. The imaging panel according to claim 11,
wherein the thin film transistor further includes a second insulating film covering the semiconductor active layer, and
wherein the first insulating film and the second insulating film include a silicon oxide film contacting the semiconductor active layer.

17. The imaging panel according to claim 1, wherein the reflective electrode is integrally formed with the drain electrode as an extension thereof.

* * * * *